United States Patent
Kipouros (10) Patent No.: US 8,926,823 B2
(45) Date of Patent: Jan. 6, 2015

(54) SUB-COATING COATED METAL CORROSION MEASUREMENT

(76) Inventor: Georges J. Kipouros, Bedford (CA)

( * ) Notice: Subject to any disclaimer, the term of this patent is extended or adjusted under 35 U.S.C. 154(b) by 171 days.

(21) Appl. No.: 13/289,585

(22) Filed: Nov. 4, 2011

(65) Prior Publication Data

US 2012/0132541 A1 May 31, 2012

Related U.S. Application Data (60) Provisional application No. 61/418,035, filed on Nov. 30, 2010.

(51) Int. Cl.
*G01F 1/64* (2006.01)
*G01N 17/04* (2006.01)
*G01N 17/02* (2006.01)

(52) U.S. Cl.
CPC ...................................... *G01N 17/02* (2013.01)
USPC ........................................ 205/776.5; 204/404

(58) Field of Classification Search
CPC ..... G01N 17/02; G01N 17/04; G01N 17/043; G01N 17/046
USPC ........... 205/775.5, 776.5; 324/700, 721, 71.2; 204/404
See application file for complete search history.

(56) References Cited

U.S. PATENT DOCUMENTS

| | | | |
|---|---|---|---|
| 3,479,256 A | 11/1969 | Smith et al. | |
| 3,593,118 A * | 7/1971 | Chaney et al. | 324/442 |
| 3,878,064 A | 4/1975 | Weisstuch et al. | |
| 4,056,445 A | 11/1977 | Gauntt et al. | |
| 4,294,667 A | 10/1981 | Yamamoto et al. | |
| 4,395,318 A * | 7/1983 | Tait et al. | 204/404 |
| 4,800,165 A * | 1/1989 | Oka et al. | 205/777 |
| 4,863,571 A | 9/1989 | Chambaere | |
| 4,863,572 A | 9/1989 | Jasinski | |
| 5,188,715 A | 2/1993 | Chen et al. | |
| 5,529,668 A * | 6/1996 | Hall | 205/776.5 |
| 5,698,085 A | 12/1997 | Yu | |
| 5,795,461 A | 8/1998 | Rising | |
| 5,888,374 A | 3/1999 | Pope et al. | |

(Continued)

FOREIGN PATENT DOCUMENTS

JP 62259052 A * 11/1987

OTHER PUBLICATIONS

Szumilak, Aaron, PowerPoint Presentation titled, "Electrochemical Behavior of the Semi-Integrated Electrode", dated Nov. 30, 2009.

(Continued)

*Primary Examiner* — Luan Van
*Assistant Examiner* — Maris R Kessel
(74) *Attorney, Agent, or Firm* — Woodard, Emhardt, Moriarty, McNett & Henry LLP (57) ABSTRACT

A system and method for generating and collecting data to detect and evaluate corrosion in a conductive metal beneath a protective coating is disclosed. A semi-integrated electrode having a reference electrode and a counter electrode is connected to a portable hand held device, such as a portable potentiostat generator. That device is also connected electrically to the metal being evaluated with the metal forming a working electrode. The counter electrode is physically and electrically separate from the metal, and a signal or voltage potential is provided therebetween through an electrolyte solution, such as sea water. The system and method is practiced without need for a container for an electrolyte solution. Data are collected and displayed indicating corrosion.

18 Claims, 8 Drawing Sheets

(56) References Cited

U.S. PATENT DOCUMENTS

| | | |
|---|---|---|
| 6,365,034 B1 | 4/2002 | Spellane |
| 2005/0274611 A1 | 12/2005 | Schlichting |
| 2008/0128294 A1* | 6/2008 | Dunn et al. ................ 205/775.5 |

OTHER PUBLICATIONS

Stephenson, L.D.; Kumar, Ashok; Hale, Jeremy, "Sensor System for Measurement of Corrosion Under Coatings" MP Materials Corrosion Prevention and Control Worldwide, May 2009, pp. 36-41.

"Wet Sponge Holiday Detectors Operating Instructions", Pipeline Inspection Co., Ltd. Nov. 10, 2003.

Heffernan, Virginia, "Illuminating Wear With Composite Electroless Nickel Coatings", Industry 2.0—Technology Management for Decision-Makers, Jun. 2010, p. 28.

Szumilak, Aaron, "Electrochemical Study of the Semi-Integrated Electrode", Nov. 30, 2009.

* cited by examiner

SUB-COATING COATED METAL CORROSION MEASUREMENT

CROSS-REFERENCE TO RELATED APPLICATION

This application claims the benefit of U.S. Provisional Application No. 61/418,035 filed Nov. 30, 2010, which is hereby incorporated by reference.

BACKGROUND

The present invention relates to detecting and measuring corrosion, and more specifically measuring corrosion in a metal beneath a coating.

The annual cost of corrosion is presently estimated at upwards of U.S. $300 billion. Currently the oil and gas sector alone estimates the cost of corrosion at approximately U.S. $50 billion annually. Recent highly publicized failures of oil carrying infrastructure in North America have demonstrated that such incidents can have dramatic effects on the environment and even lead to the loss of life. To protect the environment and fuel assets new sophisticated monitoring systems are required. Efforts to mitigate the ongoing problem of corrosion in the oil and gas sector are spent primarily in the production of corrosion resistant paints and coating. An estimated $27 billion dollars is spent on the development and testing of new products alone, while the remaining $23 billion is divided between the cathodic protection and maintenance of existing infrastructure, the development of new corrosion resistant alloys, and materials inspection and testing. Failures of components in marine environment are common. However, field-monitoring systems are invariantly somewhat ineffective at identifying corrosion under insulation (CUI). The application of these instruments results in electrochemical noise (ECN) which must be further analyzed by indirect mathematical methods to detect a potential action.

Furthermore the application of protective coatings and the life endurance of such coatings are often unpredictable. Normally failure of a component begins with the failure of the paint protective coating which compromises the exposure of the component to the corroding environment. Ironically, to prepare better coating techniques may require the advancement of better field monitoring systems by which the gradual degradation of the paint coating and the onset of the corrosion are correlated. The proper design and selection of coating systems that are applied to piping and vessels, prior to installing the insulation, have been major components in controlling corrosion under insulation. Another factor for the marine industry in preventing and controlling corrosion problems is the development of timely and reliable inspection techniques to detect corrosion under insulation, and to detect deterioration to insulation and associated sealing materials. An aim of the corrosion engineer is to reduce the intensity and extent of the corrosion process with the application of cost effective corrosion monitoring and maintenance programs throughout the useful life of an offshore or other structure. At the present time, corrosion under insulation represents an important problem for the marine industry. Effective detection and prevention of corrosion under insulation can represent a significant capital cost saving for a project.

Thus, there is a need for improvement in this field.

SUMMARY

The invention is set forth in the claims, and only the claims. This may include one or more of the following acts and/or elements of s system. For example, this may include a method for signal generating and collecting data to detect and evaluate corrosion in a conductive metal subject beneath a protective coating. This may comprise the acts of providing a signal generator, attaching a metallic conductor to said conductive metal subject to electrically connect it to said signal generator while it is in sea water outside of any container, providing a counter electrode electrically connected to said signal generator and a reference electrode electrically connected to said signal generator, positioning said counter electrode and said reference electrode assembly in an said sea water, wherein said carrier and said counter electrode and said reference electrode are positioned not in direct physical contact with said conductive metal subject, and, providing an electrical signal through said sea water between said metal subject and both said counter electrode and said reference electrode, collecting data from said electrical signal. This may be done outside of a container. It may be in the sea, but instead may be elsewhere. It may be done with or without a sponge or other electrolyte carrier.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

1. System and Method Description

Figure 1:
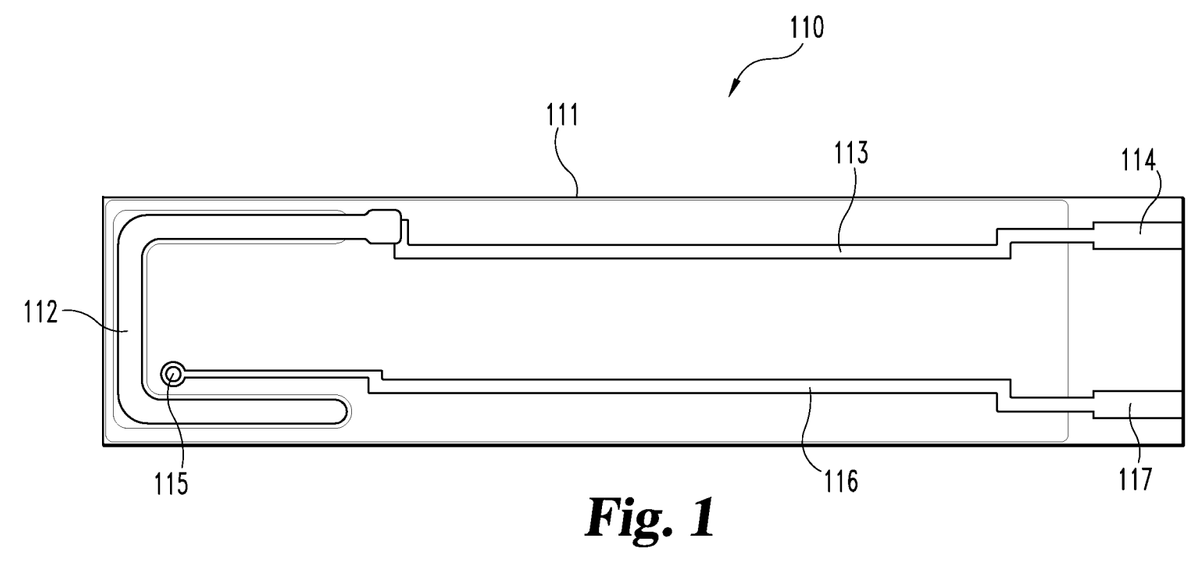
FIG. 1 is a plan view of a first example of an electrode for use in the present invention.

FIG. 1 shows one example of an electrode unit 110. Preferably it comprises a carrier 111, such as for example a printed circuit board 111, with various electrode conductors thereon and/or therein. They include electrode 112 electrically (conductively) in contact with trace 113 which itself ends in or is electrically in contact with connection or contact 114. Likewise, a reference electrode 115 may be provided on the circuit board (although optionally it may be on another circuit board or other structure). Reference electrode 115 is electrically in contact with trace 116 which in turn is electrically in contact with connection 117. Electrode, trace and connection may, and preferably are, concurrently formed of common metal (copper, gold, or other conductive metals or materials, or alloys or combinations thereof). The same is preferably true of electrode 112, trace 113 and connection 114.

Electrode unit 110 comprises, in this system, the counter-electrode. It may comprise metal (described above) with a layer of carbon or other materials thereover to facilitate electrolysis. Counter electrode 110 is electrically connected to wire 120 (see FIGS. 5 and 6) to transmit signals to reader 400. Reference electrode 115 is electrically connected to wire 130 (see FIGS. 5 and 6) to transmit signals therethrough, again to reader 400. Electrode unit 110 is semi-integrated, meaning that it does not include on it any (or any active) working electrode.

Preferably, with reference electrode 115 and counter electrode 112 on the same printed circuit board, they are spaced apart but are close to each other. The spacing may vary but preferably is less than 100 mm, more preferably less than 10 mm, and may be within about one millimeter of spacing between electrodes 112 and 115. As described more below, for example, the counter electrode may comprise a carbon layer over copper, and the reference electrode may comprise a silver layer over copper.

Figure 2:
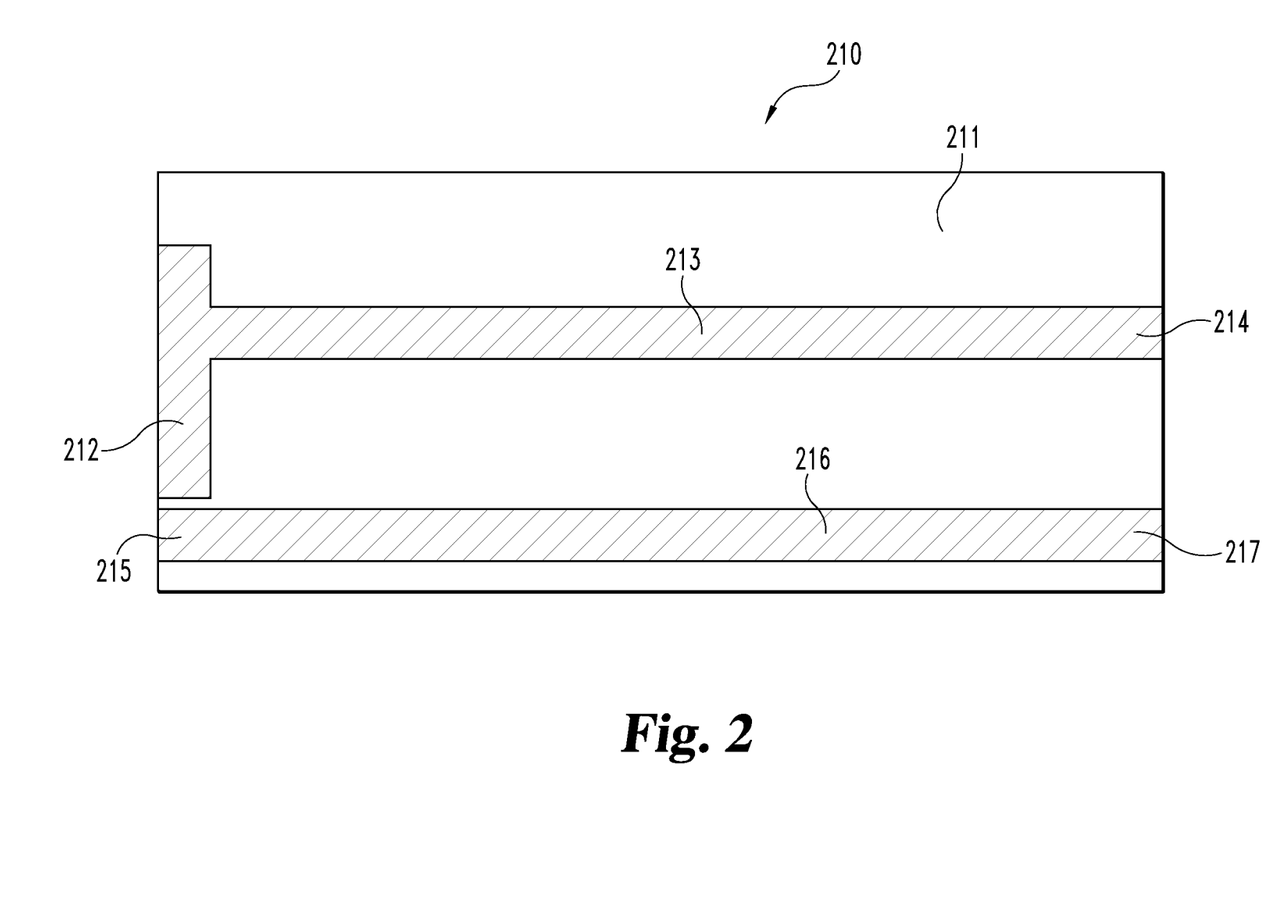
FIG. 2 is a plan view of a second example of an electrode for use in the present invention.

The size, shape, geometry of the electrode unit may vary. FIG. 2 is an example, varying as shown from the unit of FIG. 1. Note that the electrode unit of FIG. 2 (drawn to scale, with a length of about 60 mm and a width of about 15 mm) is the electrode unit actually used in the tests, described below in this application. It comprises unit 210 with carrier, a printed (non-conductive) circuit board 211. On the circuit board is a conductive layer including counter electrode 212, trace 213 and connection or contact 214. Another conductive layer comprising reference electrode 215, trace 216 and connection 217 is also provided. As described more below, for example, the counter electrode may comprise a carbon layer over copper, and the reference electrode may comprise a silver layer over copper. The width of the traces 213 and 216 are about 3 mm, but may be wider and/or narrower, and the electrode 212 may, as shown, be about the same, and also may be narrower or wider. Like unit 110, electrode unit 210 is semi-integrated, meaning that it does not include on it any (or any active) working electrode.

Through simple printed circuit board manufacturing techniques an electrode unit, such as units 110, 210 or otherwise, may be used comprising a semi-integrated electrode. The boards may be resin based or other plastic or ceramic, or otherwise. Preferably, for manufacturing cost considerations they are flat and thin (about one millimeter), although they may be rods, tubes or other geometries with printed circuit traces and contacts and electrodes thereon or therein.

Figure 5:
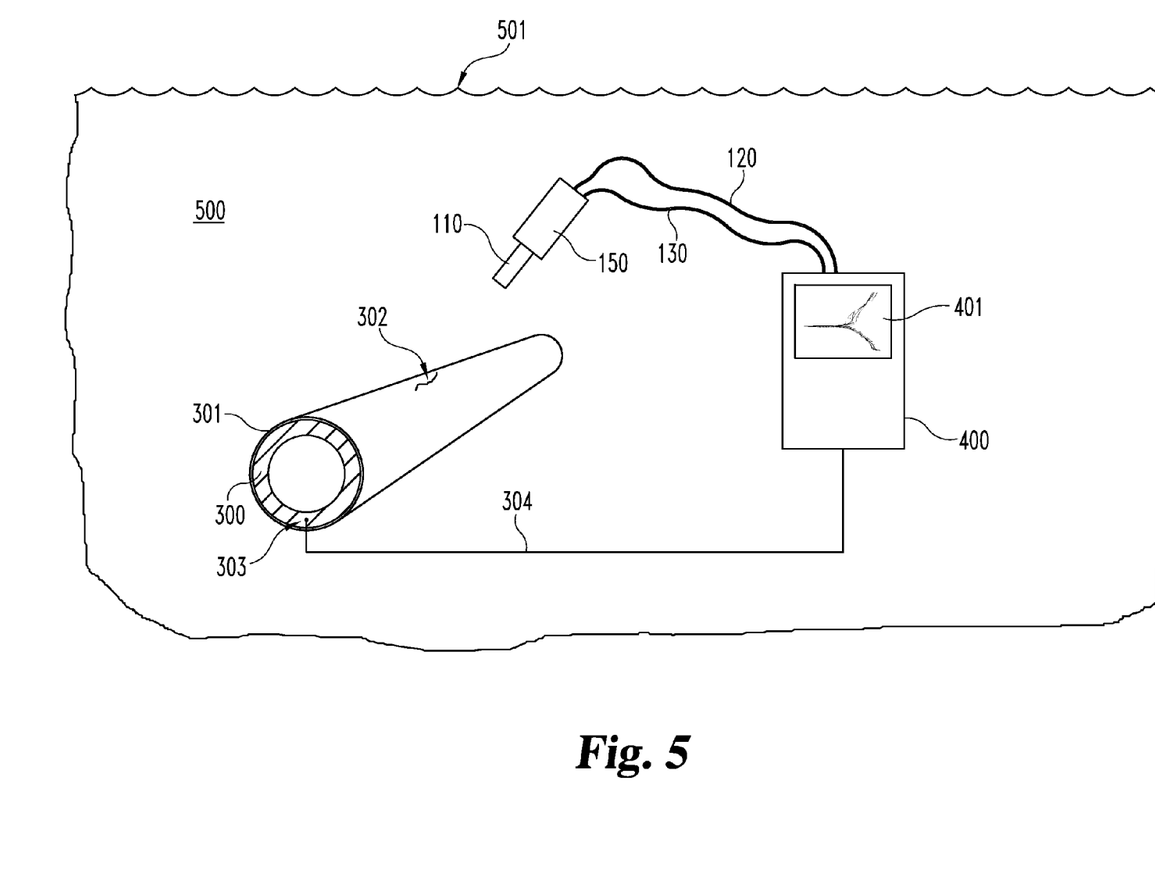
FIG. 5 is a schematic drawing of the present invention undersea.
Figure 6:
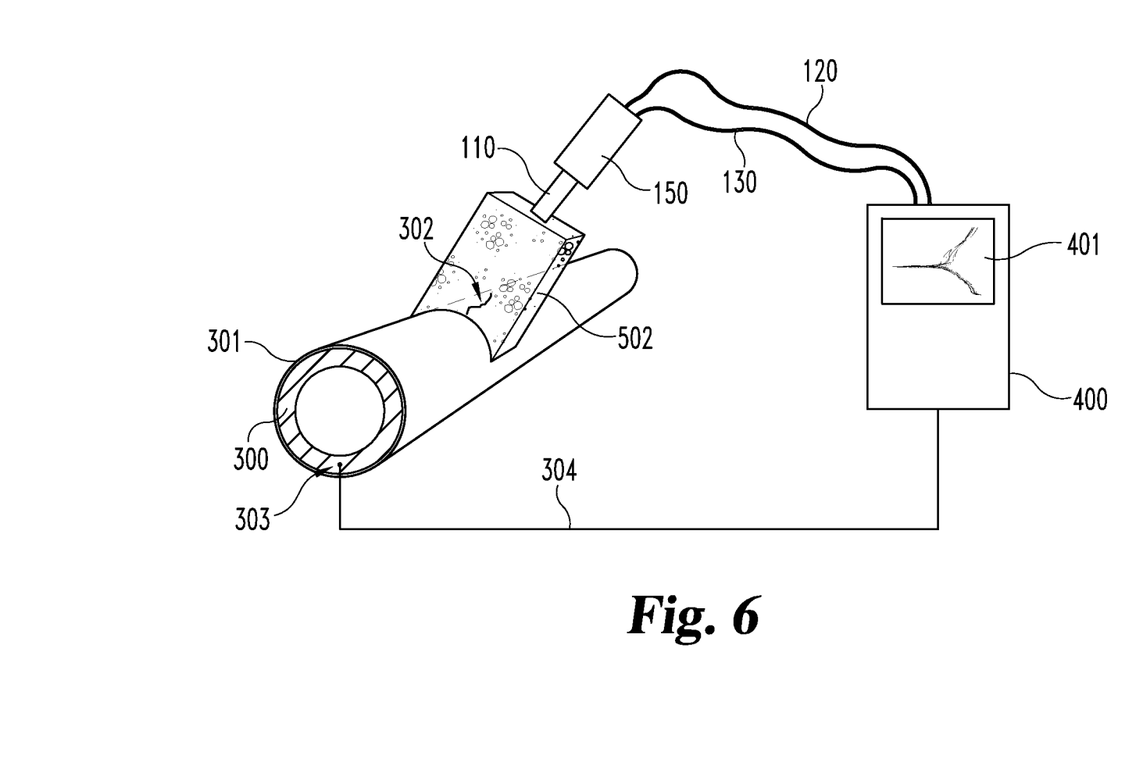
FIG. 6 is a schematic drawing of the present invention using an electrolyte solution carrier.

FIG. 5 and FIG. 6 illustrate, schematically, different examples of the system and method of the present invention.

Referring to FIG. 5, the system is shown in a natural sea water 500 environment defined by sea level 501. This is in field conditions, such as the ocean, and is not in a test cell. Notably, the system and method are not within a container. Within that environment 500 is a conductive metal subject 300 beneath a protective coating 301. As mentioned, subject 300 may be steel pipe or otherwise, and coating 301 may be paint or an epoxy coating or otherwise. A sensor or meter 400 is provided. Typically, device 400 may comprise a potentiostat, described further below. Note that although this is illustrated as being under water, it may be out of the water as well. Sensor 400 is connected by conductive wire (normally insulated) 304 at connection point 303 to subject 300. Hence, there is an electrically conductive contact between metal subject 300 and device 400. Additionally, device, such as potentiostat 400, is electrically connected to probe 150 by electrically insulated wires 120 and 130. An electrode unit 101, as previously described, is inserted in probe 150. In this respect, probe 150 may have a slot or other opening for receiving probe electrode 110. Of course, electrode unit 210 or otherwise may be used in addition to or in lieu of unit 110. Within probe housing 150 our electrical connections that by squeezing other friction fit provide electrical conductivity between wire 120 and connection 114 and/or 214 as previously described. Likewise, wire 130 is electrically connected by pressure or squeezing or friction with connection 117 and/or 217 as previously described. As illustrated, wires 120 and 130 are electrically insulated, isolating them from sea water 500 just as wire 304 is isolated from sea water 500. Wires 120 and 130 may be in a common insulation conduit with each other. Alternatively, sensor 400 may be integrally formed in a common housing with probe 150. Such integrated housing was preferably compact and portable and handheld. In either event, probe 150 is preferably compact and portable and handheld. Such portable handheld feature allows for field testing. This field work may be done on or below ground, or below water such as by scuba divers, subs, robots, or otherwise. Sensor 400, when physically separate from probe 150, can be located in a boat or on another surface outside of water 500 with long wires electrically connected to the working electrode (e.g. metal member 300) and to the semi-integrated electrode/sensor 110 which is in sea water 500. Electrode units 110 and/or 210 may simply, conveniently plug into or slide into probe 150 much as the printed circuit board used for diabetes glucose monitoring may be slid into such a unit. They may be conveniently and quickly replaced, in the field and even in a scuba diving operation.

Probe 150 and/or housing 400, as appropriate, are built to be otherwise sealed from or prevented from damage by sea water 500. This optionally includes having one or both units made primarily of plastics, ceramics, and/or non-corrosive metals, such as stainless steel, gold or the like. A small penetration 302 is formed in protective coating 301. Such penetration 302 may be a pin prick, a small scratch, or otherwise. It may be pre-existing, although it is penetration normally is created by the operator(s). As illustrated in FIG. 5 (and in FIG. 6), the electrode unit 110 is physically and electrically separate from the metal conductor subject 300. It is positioned not in direct physical contact, and yet within a proximity of the scan distance or interval, described elsewhere in this application. For example, such scan distance may be 20 cm, 60 cm, or greater (or less). Sea water 500 provides an electrolytic solution between electrode unit 110 and penetration 302 providing access immediately thereunder to metal subject 300. In this way, metal subject 300 acts as a working electrode, with the counter-electrode in unit 110 having a voltage potential between such counter electrode and such working electrode. By providing a voltage potential, such as a voltage sweep with the signal of voltage and current track (see for example, FIGS. 3A, 3B, 3C, 4), corrosion data may be collected and provided on at least one display.

For example, display 401 on sensor or meter 400 is depicted. Note, however, display 401 is merely symbolic, and may take a variety of forms. For example, display 401 may be a graphic Tafel plot (or other plot) as illustrated. Although, it also may be one or more digital read-outs, print-outs, corrosion values as translated from the data or otherwise. It may also be simply a electrical data transmission to another computer or display unit that is remote from sensor 400 and/or may be copied to electronic recordable media, such as a compact flash card or otherwise, for immediate or subsequent uploading or other use to a computer or other display of the collected data. Counter electrodes and reference electrodes of electrode unit 110 are inserted and/or immersed in solution 500 in the field in proximity of pipe 300 and its opening 302.

To obtain an electrochemical signal we need (a) two at least electrodes, (b) an ionic electricity conducting medium (electrolyte) and (c) no insulator in between them. If (a) (b) (c) are not fulfilled no signal can be obtained. So, a steel pipe 300 in sea water and a perfect insulator placed on the pipe no corrosion and no signal. When the insulator shows imperfection, defect or crack we have electrical contact and the (EXTERNAL) corrosion begins on the outside the pipe. To avoid (INTERNAL) corrosion the inside of the pipe is also insulated and to fight the onset of the internal corrosion chemicals (inhibitors) are used. Monitoring the pipelines is required for the presence of external and internal corrosion.

To measure the loss of material due to corrosion per year an electrochemical technique is used called Tafel extrapolation which determines the corrosion rate:

$$\text{Corrosion Rate(CR)} = Ka \, i_{corr}/nd \quad (1)$$

where

Figure 3A:
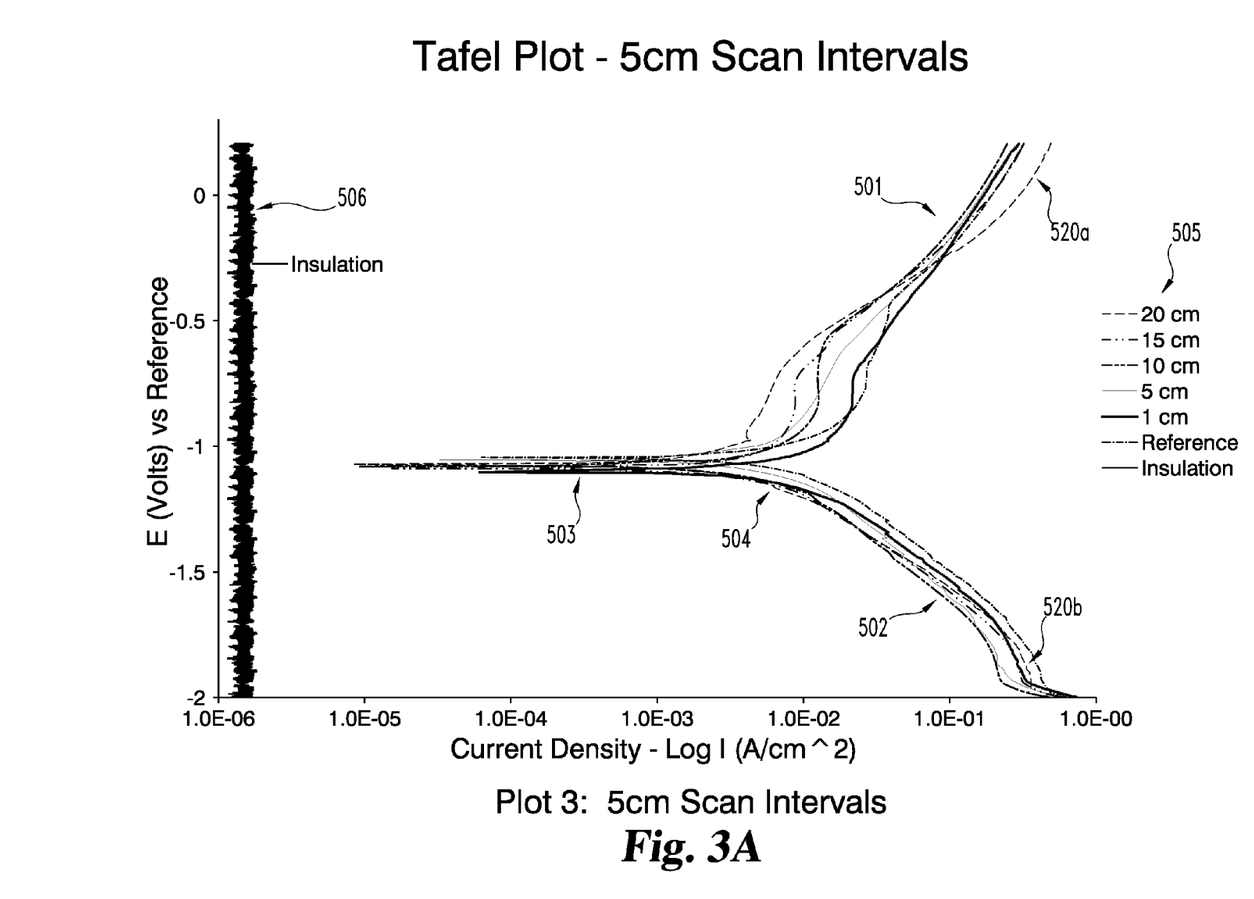
FIG. 3A is a sample Tafel plot showing voltage-current density for various scan distances between the counter electrode and the subject and for the reference electrode.
Figure 3B:
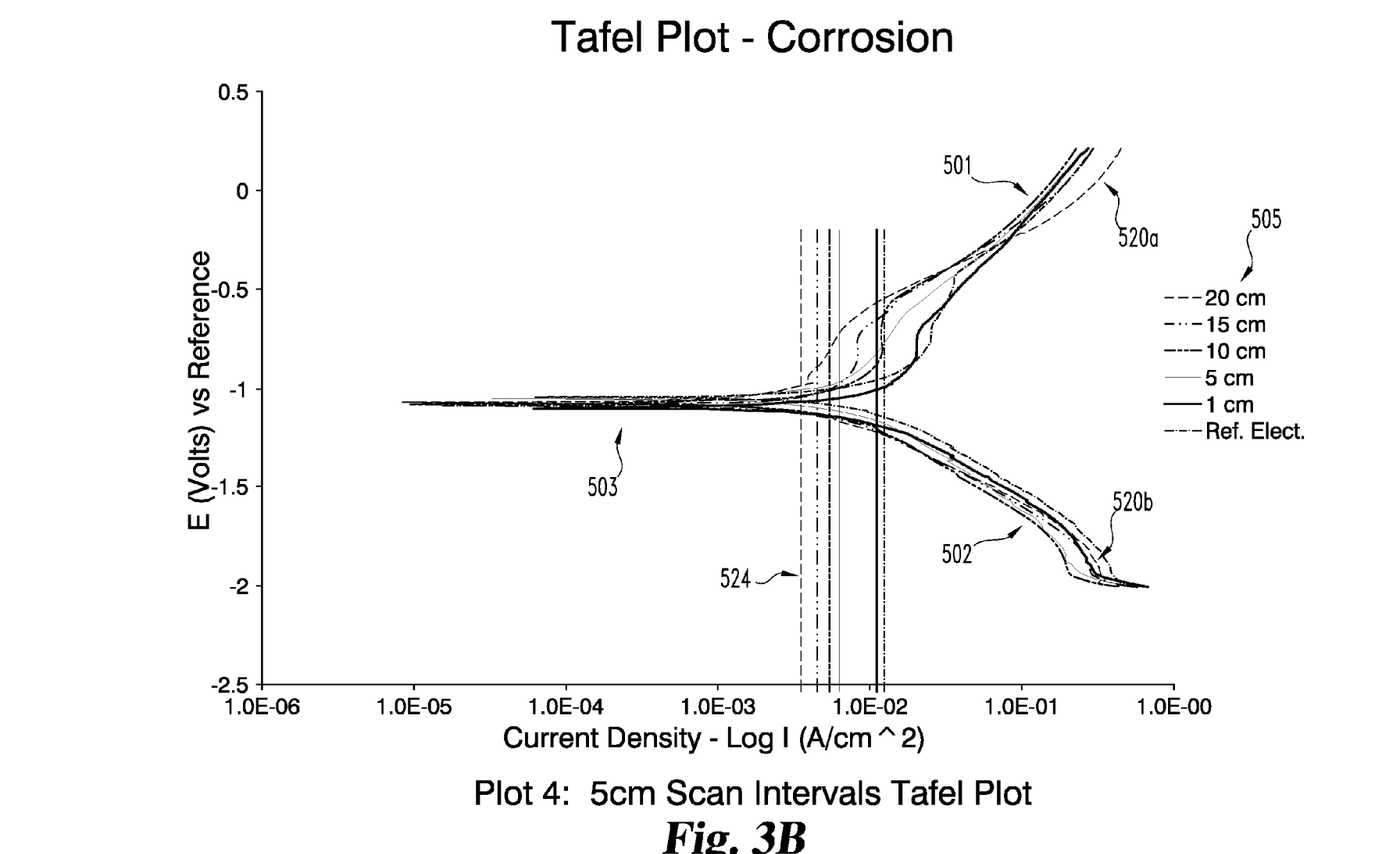
FIG. 3B is a Tafel plot of 3A with vertical lines projecting current density readings.
Figure 3C:
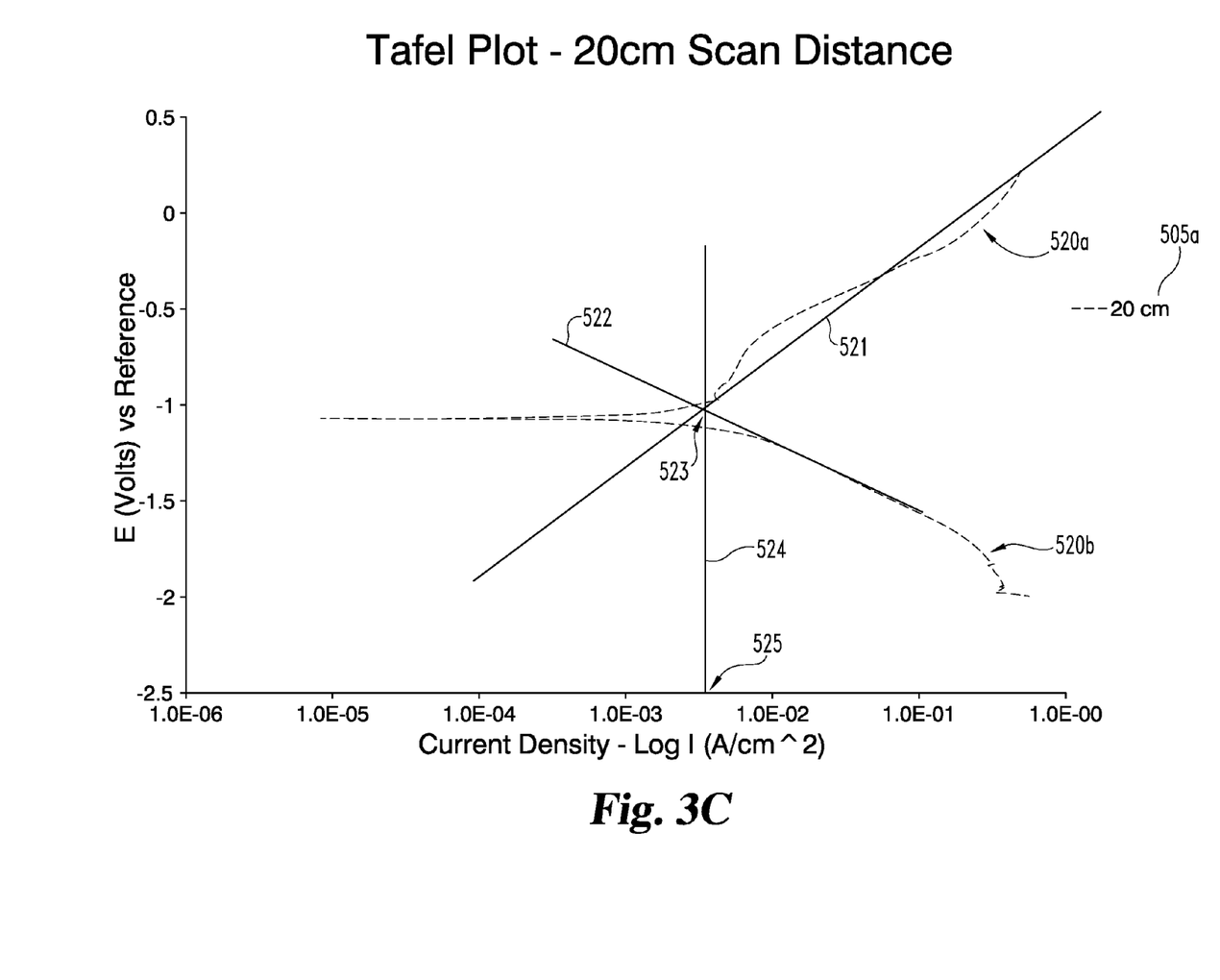
FIG. 3C is a Tafel plot showing the 20 cm scan distance as plotted in FIGS. 3A and 3B.

K: a constant and its value depends on the unit used for expressing the corrosion rate a: the atomic weight of the corroding metal $i_{corr}$: the corrosion current in $\mu A/cm^2$ n: is the number of electrons lost due to corrosion d: is the density of the metal in $g/cm^3$ FIGS. 3A, 3B, 3C and 4 are examples of Tafel plots from the present invention. To perform Tafel extrapolation a linear change of the potential with time is applied between the working electrode and the reference electrode. The resulting data are recorded on a log (i) [current density] vs. E [potential] plot which is called Tafel plot as shown in FIG. 3C. The corrosion current, $i_{corr}$, and the corrosion potential, $E_{corr}$, are obtained from this technique. The corrosion rate is calculated from the corrosion current ($i_{corr}$) using the equation above.

To perform this technique or any other electrochemical technique an instrument called potentiostat may be used. But one example is a Princeton Applied Research (PAR) Model 273A potentiostat. The potential between the working electrode (steel pipe corroding) and the reference electrode is programmed to vary linearly with time. As the instrument tries to do that the real potential between the working and the reference varies. It becomes necessary to allow current to flow from the steel (working electrode) to carbon (counter electrode) to try to keep the potential in linear function with time. Therefore the resulting real potential varies with the current and this is recorded by the potentiostat. However, if the reference electrode is far away or broken the signal becomes an electrochemical noise (ECN).

Electrochemical techniques for the determination of corrosion rates are normally directed to the measurement of $I_{corr}$ from which the corrosion current density $i_{corr}$ can be determined. The corrosion current density ($i_{corr}$) can be easily determined from the corrosion current ($I_{corr}$) divided by the surface area (A) of the working electrode per the equation:

$$i_{corr} = \frac{I_{corr}}{A}$$

From the value of corrosion current density determined from the Tafel plot extrapolation, the equations below can be employed to determine the corrosion rate intensity (CI) and the corrosion penetration rate (CPR) describing the amount of mass from the working electrode lost per year Corresosion intensity:

$$CI(g/m^2 * y) = 0.327 \frac{M * i_{corr}}{m}$$

Where, the corrosion intensity is measured in grams per meter squared per year. M=is the atomic mass of the corroding material; $i_{corr}$=the corrosion current density (mA/m2); m=the mass of the working electrode. Corrosion penetration rate may be expressed in the equation:

$$CP(mm * y) = 0.327 \times 10^{-3} \frac{M * i_{corr}}{m\rho}$$

Where,

M=is the atomic mass of the corroding material $i_{corr}$=the corrosion current density (mA/m$^2$)

m=the mass of the working electrode $\rho$=is the density of the material in question The present invention is not limited to using a potientiostat and/or Tafel extroprolation or Tafel plots. Any electrochemical technique (ECT) can be used with the sensor 400 that will give a clear signal. Such ECT's include, but not limited to, linear sweep polarization (LSP), cyclic polarization (CP), cyclic voltammetry (CV), electrochemical impedance spectoscopy (EIS), variations and hybrids thereof, and others. The following Table 1 sets forth some alternative electrochemical techniques usable as part of the present invention, and some of their attributes with numbers reflecting the applied potentials versus a saturated calomel electrode (SCE) as reference for the study of corrosion of copper nickel alloys in sea water:

TABLE 1

| Electrochemical Techniques | | | |
|---|---|---|---|
| Electrochemical Techniques | Applied | Plots | Results |
| Linear Sweep Polarization (LSP) | Potential −0.25 to +0.75 V/SCE | E vs. log (i) | Passivation and transpassive potentials |
| Cyclic Polarization (CP) | Potential cycled from −1.5 to +2.5 V/SCE | E vs. log (i) | Corrosion and protection potential |
| Tafel Extrapolation (TE) | Potential −0.5 to 0.02 V/SCE | E vs. log (i) | Corrosion rate |
| Cyclic Voltammetry (CV) | Potential cycled −1.5 to 1.5 V/SCE | E vs. (i) | Electrochemical reactions nature |
| Electrochemical Impedance Spectroscopy (EIS) | AC of 10 mV and frequency range of (0.2 Hz to 60 kHz) | Real vs. imaginary impedance (Z'/Z") | Number and thicknesses of passive films |

The counter electrode (for example 112 or 212) may generally be made of a material which will support the conduction of electricity but itself will not be reduced thereby contaminating the system; for example high density graphite or platinum. The controlling potentiostat 400 generally has an open circuit potential readout where the voltage of the connected system can be determined. The open circuit potential is a representation of the working electrodes desire to spontaneously corrode in the specified system. The controlling potentiostat can then be set to polarize the working electrode either anodically, where oxidation is occurring on the surface of the electrode, or cathodically where the surface of the working electrode is being reduced. As the potentiostat alters the potential above the open circuit potential an anodic polarization curve is generated; conversely as the potential is lowered below the open circuit potential, a cathodic polarization curve is generated. Parallel lines 521 and 522 (see FIG. 3C) superimposed on to the polarization curves to determine the corrosion potential $E_{corr}$ and the corrosion current $I_{corr}$ (see 525 in FIG. 3C) is the basis of the Tafel extrapolation. The intersection of the linear lines applied to both the anodic and cathodic polarization curves yields values for $E_{corr}$ and $I_{corr}$. A potential scan rate of ±300 mV/s can be employed to produce a linear section on the polarization curve to produce a relatively accurate extrapolation of $E_{corr}$ and $I_{corr}$. Greater or lesser scan rates may be used as well.

This invention may be used in many industries including pipelines, conduits, ships, outdoor equipment, underwater equipment, harbor gates, walls and other structures, pumps, turbines and offshore structures, to name a few. For example, topsides of offshore gas producing installations are very vulnerable to this type of degradation. Erosion is a mechanical wear process due to both fluid flow and particulate matter abrasion. Like abrasion, erosive wear can involve both plastic deformation and brittle fracture and it is affected by the hardness, elastic modulus and toughness of the coating and the solid particles in the stream. The operative wear mechanism(s) depends on both mating materials involved and the condition of impact, primarily particle mass, shape, velocity, and impingement angle. It is expected that simultaneously or in an interrupted manner the corrosion sensor will help to investigate the onset of erosion on the marine and other assets. This may be applicable to all marine infrastructures which are exposed to the effect of sea water. Direct application of the proposed corrosion sensor is intended for coated surfaces that are immersed in sea water or are wetted by sea water in a way that allow electricity to pass through coating defects. Applications will also include surfaces covered with corrosion protective coatings which are also covered by concrete. Simple modification of the sensor, which will be developed on this proposal, will allow the application of the sensor to surfaces which although are not immersed in sea water can be made wet with an artificial agent such as a wet sponge.

A highly sensitive semi-integrated electrode 110, 210 is provided to detect the occurrence of corrosion. The efficiency of this system will result in a clear electrochemical signal instead of the electrochemical noise (ECN) mentioned previously. The sensor provides clarity of the signal which will remove the ambiguity on the onset of localized corrosion. Because the signal is clear, the method of detection is direct and does not need further mathematical manipulation, although optionally this may be done to the results.

The item which is painted or coated and needs inspection will be made one part of the electric circuit and the semi-integrated sensor will complete the circuit. The metallic piece to be tested will be the part that the semi-integrated electrode, the sensor, is missing in order to function. As the sensor detects the missing part through the electrical connectivity the position of the corrosion site will be accurately detected by providing the path for electrochemical action (i.e. corrosion).

It is also envisioned that coatings and paint manufacturers will use the sensor to ensure that items coated by FBE (Fusion Bonded Epoxy) and/or paint are well adhered to the substrate not allowing corrosion degradation. Inspection and monitoring of subsea pipelines, gas and oil production platforms and topsides, buildings with supports in the seawater will be more accurate with the new sensor. Land-based infrastructure the failure of which causes severe environmental catastrophes such as industrial and home oil tanks may be inspected using the sensor. In addition, through simple printed circuit board manufacturing techniques, disposable sensors of small dimensions can be manufactured which may be used in combination with handheld electrochemical equipment such as a PG581 Portable potentiostat/galvanostat, handheld with USB to PC interface available from Advance-Tech. In general, all coated and/or painted metallic structures are potential applications for the proposed corrosion sensor device, whether the inspection personnel is a highly trained individual employed by a corporation or the person is an individual who can perform the simple test. No high voltage is normally required.

Using this approach, the electrochemical noise will be greatly reduced or eliminated.

2. Experimental Procedures

The following section in divided into five sub sections representing each of the bench tests conducted and manufacturing methods used to create a prototype electrode of the type illustrated in FIG. 2. The first two sections below outline the tests conducted to evaluate the performance of the Pine instruments integrated electrode in the electrodeposition of Nickel and to determine the effects of surface area on current density. The third section outlines the manufacturing methods used to fabricate the prototype semi-integrated electrode and last sections outlines the bench tests conducted to evaluate the performance and sensitivity of the prototype electrode with steel in salt water.

2.1. Electrodeposition of Nickel in Pine Cell.

The following experiment was used as a baseline test and a stepping stone to learn how the Pine integrated electrode functions under potentiostat control. This experiment is offered from Pine instruments as teaching aid. A standard Watts nickel plating was prepared from 290 g of nickel sulfate hexahydrate, 30 g of boric acid, and 8 g of sodium chloride per liter. Approximately 20 ml of nickel plating solution is poured into the scintillation vial. The electrode is plugged into the plastic grip assembly, the cap is secured and the assembly inserted into the plastic molded cap. A simple grip style ring stand assembly is used to hold the scintillation vial in place during the experiment. Vial is connected to the potentiostat via the external electrometer. The potentiostat is controlled though the windows based software CorrWare. The experiment is run as a potenitostatic experiment and the potential is held at −1.2V versus the Ag/AgCl reference electrode for 90 s. The output potential and current data is saved in the location specified by the user and can be accessed for review though the windows based software CorrView. From the output data the quantity of electricity applied can be determined for the experiment though the integration of the i-t plot generated.

2.2. Electrodeposition of Nickel with External Electrode—Area & Current Density.

This experiment utilized a polyurethane cast external graphite electrode in conjunction with the Pine integrated electrode. The working electrode on the pine integrated electrode is removed from the system simply by not connecting it to the electrometer via the red banana jack. The external electrode was manufactured using a ¼" thick section cut from a ½" Ø 1010 mild steel rod. A small hole was drilled into the side of the steel puck and a polymer coated copper wire was connected to the electrode by solder. The steel electrode was then placed in a small plastic cap and covered with polyurethane resin. The resin was allowed to cure for 12 hours prior to use. Prior to use the conductivity of the electrode was tested using a multi meter to ensure an adequate electrical connection is achieved. Once the resin fully cured, the electrode was polished using 800 grit sandpaper and machined down to fit in the pine instruments scintillation vial.

Again a standard Watts nickel plating bath was prepared using 290 g of nickel sulfate hexahydrate, 30 g of boric acid, and 8 g of sodium chloride per liter [6]. Approximately 20 ml of nickel plating solution is poured into the scintillation vial and held at −1.2V versus the Ag/AgCl reference electrode for 90 s through the control of the potentiostat. The external electrode is inserted into the scintillation vial prior to connection to the electrometer. The external electrode was placed approximately 3 mm from the Pine integrated electrode and is positioned facing the pine electrode. This particular experiment was repeated three times while reducing working electrode area by masking and coating the original electrode with non-conductive paint. The area was reduced from 0.785 cm 2, to 0.38 cm 2, then to 0.031 cm 2 and tested. The effect of varying external working electrodes area was quantified by measuring the deposited nickel mass each time to determine the electrodeposition efficiency.

2.3. Manufacturing Prototype Semi—Integrated Electrodes.

The methodology followed for the fabrication of the prototype electrode was that of simple printed circuit boards (PCBs) shown in FIG. 2. A one sided 8"×11" copper clad board was purchased. The design for the electrode was laid out in AutoCAD brand software and all areas to remain copper clad are blacked out in the line drawing. The electrode design was duplicated and laid out such that twenty electrodes could be manufactured from the single PCB board in a single session. The multiple electrode layout design was printed onto high gloss laser photo paper at the highest quality settings. Since laser printers melt tiny plastic beads on to the paper when printing it serves as a perfect means to provide an accurate mask of the PCB board from etchants later in the process. The printed electrode photo paper layout is placed face down on the PCB board and ironed at the highest heat setting for approximately ten minutes. Specific attention to areas of minuscule features should be carefully pressed as not to smudge or smear the plastic as it melts onto the PCB.

Once completed, the board and adhered photo paper is immersed in cold water until saturated so it can be easily removed. The board with the transferred electrode design is then gently cleaned by hand to remove any excess paper. The etchant is prepared from 250 g/l of ferric chloride. A heated etchant bath at 75° C. is prepared and the masked PCB is immersed for 20 min. to remove the exposed copper leaving the masked areas behind. The plastic masking is then removed with acetone and cleaned thoroughly. Individual electrodes are separated from the 8"×10" sheet using a metal press shear. The electrodes are collected and cleaned again using steel wool and acetone. Conductive carbon adhesive is applied to the counter electrode with a fine paint brush and dried in air at room temperature for 20 min. Once fully dry a careful inspection of the surface is made to insure that all of the copper backing is fully covered. If any small area of the copper backing is still visible a second coat is re-applied to insure that the electrode will not bypass the carbon electrode normal operation. The reference electrode is made by mixing fine chloride powder with a silver conductive adhesive and applied to the electrode. Again a 20 min. drying time was used before handling. The remaining exposed copper surfaces (leaving 5 mm at the top of the electrode for contact purposes) are insulated from the system using a silicone insulating adhesive. The silicone adhesive is permitted to cure for 24 hrs at room temperature prior to use. The electrodes are connected to the system via a simple edge board connector which has wires soldiered to the applicable connection. This particular example of how to make electrode 210 is not limiting, and the invention may be conducted using any of hundreds of manufacturing techniques, including without limitation known circuit board manufacturing techniques.

2.4. Electrode Sensitivity Tests in Salt Water.

A 25 cm×18 cm clear plastic tray was filled with 1 L of synthetic salt water. A metric ruler was placed below the tray to accurately quantify the sensitivity of the electrode vs. the distance from the corroding working electrode (or distance from the defect). The external electrode was manufactured from a ¼' thick section cut from a ½' Ø plain carbon steel rod. A small hole was drilled into the side of the steel puck and a polymer coated copper wire was connected to the electrode by solder. The steel electrode was then placed in a small plastic cap and covered with polyurethane resin. The resin was allowed to cure for 12 hours prior to use. Prior to use the conductivity of the electrode was tested using a multi meter to ensure an adequate electrical connection was achieved. Once the resin fully cured, the electrode was polished using 600 grit sandpaper then finished with 1 μm diamond paste. The working electrode was fixed at one end of the tray and the prototype was moved relative to its position. Prior to conducting this test the working electrode is masked with electrical tape and a potential sweep from −2V to 0.2V is executed. The purpose of this test is to insure that the working electrode is fully insulated from the system prior to testing. Following the successful completion of this test a 0.01 cm×10 cm scratch is induced in the insulated coating and the potential sweep from −2V to 0.2V is again executed while positioning the electrodes are 20 cm apart. The prototype electrode is moved 1 cm incrementally closer to the working electrode and the test is re-run. This process is repeated and recorded for all twenty positions between the electrodes. The output data are recorded and plotted to see how the sensitivity and response of the electrode varies with position from the corroding surface.

2.5. Sensitivity Test

The identical test to that conducted in section 2.4 was repeated for this test however the objective is to determine the sensitivity of the prototype electrode. The electrodes are separated 65 cm initially; then by 10 cm increments the distance is reduced until a reasonable approximation of the collected data from section 2.4 is achieved. Note the reference in FIG. 4 to "Max" is not a limitation on the scan distance or interval for the invention as claimed and disclosed, but rather sets forth some limits of this particular testing.

3. Experimental Results

The following section contains collected data gathered from the experiments described in the following section. The following tables below outline the data collected from the experiment outlined in section 2.2. Table 2 shows working electrode (W.E.) area and efficiency. Table 3 pertains to testing a (prior art) Pine (brand) electrode, essentially identical to electrode 110 shown in FIG. 1 but also having a working electrode printed thereon.

TABLE 2

W.E. Area and Efficiency

| Electrode Area (cm$^2$) | I (A) | T (s) | Q (C) | Before (g) | After (g) | Actual (g) | Theoretical (g) | Efficiency |
|---|---|---|---|---|---|---|---|---|
| 0.785 | 0.030 | 90.000 | 2.676 | 4.813 | 4.814 | 0.001 | 0.001 | 86.019 |
| 0.381 | 0.035 | 90.000 | 2.930 | 4.672 | 4.673 | 0.001 | 0.001 | 89.785 |
| 0.031 | 0.040 | 90.000 | 3.585 | 4.723 | 4.724 | 0.001 | 0.001 | 91.734 |

TABLE 3

Pine Instruments Nickel Electrodeposition Data

| Electrical Charge/C | Mass/g Before | Mass/g After | Mass Gain/mg Actual | Mass Gain/mg Theoretical | Efficiency (%) |
|---|---|---|---|---|---|
| 7.477 | 0.4848 | 0.4869 | 2.1 | 2.27 | 92 |
| 8.082 | 0.4775 | 0.4798 | 2.3 | 2.46 | 94 |
| 8.271 | 0.4850 | 0.4871 | 2.1 | 2.51 | 84 |
| 6.848 | 0.4784 | 0.4802 | 1.8 | 2.08 | 86 |
| 6.654 | 0.4826 | 0.4845 | 1.9 | 2.02 | 94 |
| Average Plating Efficiency | | | | | 90 |

Per Section 2.4 above, while Tafel data was collected at one centimeter intervals, for drawing clarity FIG. 3A shows the subset of results showing the reference plot, the Insulation plot 506, and plots at scan intervals (scan distances) of 1, 5, 10, 15 and 20 centimeters. In FIGS. 3A and 3B, the horizontal regions 503 converge along the voltage value (E) on the Y-axis, and the positive sloping regions 501 intersect with the negative sloping regions 502 at intersections 504. A key or legend for the scan distances is shown in FIGS. 3A, 3B and 3C as legend 505. FIG. 3B adds to FIG. 3A the vertical projections, such as projection 524, showing the current density values for each scan at the X-axis. The plot 520a is the 20 centimeter scan interval plot, which is also shown in FIG. 3C in isolation from the other plots. Note the liner line 521 (positive slope, showing anodic slope corrosion from the working electrode, e.g. steel pipe) and line 522 (negative slope, showing cathodic slope corrosion (carbon) hydrogen evolution) used to extrapolate the values of I-Corr at intersection 523, projected downwardly to the X-axis at 524 to current density value 525 in FIG. 3C.

TABLE 4

Tafel Plot Data

| Distance | Log I (A/cm$^2$) | E$_{corr}$ (V) |
|---|---|---|
| 20 cm | 5.00E−02 | −1.1 |
| 15 cm | 3.00E−02 | −1.1 |
| 10 cm | 2.50E−02 | −1.1 |
| 5 cm | 2.00E−02 | −1.1 |
| 1 cm | 9.50E−01 | −1.2 |
| Ref. Elect | 9.00E−01 | −1.1 |

FIGS. 3A, 3B, 3C and 4 show data collected from experiments using electrode unit 210. The plot contains five (5) data sets illustrating how the polarization curves change with distance, namely scan distances reflected in table legend 505a of 60, 50, 40, 30 and 20 centimeters. As with FIGS. 3A, 3B and 3C, the 20 centimeter scan distance is shown for comparative purposes as plot 520a (positive, anodic slope) and plot 520b (negative, cathodic slope).

4. Discussion of Sample Testing.

Table 1 illustrates the differences in the electrodeposition efficiency of the three electrode areas tested. The currency efficiency of the external electrode system produced results comparable to the empirical data provided by the Pine Instruments electrode in Table 3. The deviation in efficiency from the Pine data provided is well within the range of tabulated efficiencies however it can be noted that the efficiency decreases with increasing available surface area. FIGS. 3A and 3B contains collected data from the sensitivity vs. electrode distance test. Although the data appear to correlate quite well there are variations. Easily seen from FIG. 3A is the plot 506 of the insulation test data collected. The plotted data confirms the insulating layers integrity returning an erroneous signal over all scanned potentials.

FIG. 3A illustrates the correlation between decreasing detection distance and increasing current density. As the distance decreases the current density increases. As the potentiometer 400 scans from −2V to 0.2V we can see on the lower part of the polarization curve that there is an amount of noise inherent to the signal. This is due to the production of hydrogen gas on the working electrode. The signal then sways to lower values of current density there by reducing the potential for gas evolution. As the curve inflects and begins its pass to positive potentials a vertical section is noted in the plot. This vertical section (deviation from an ideal polarization curve) is due to the steel working electrodes attempt to passivate. This occurs as a fine scale of corrosion product is formed on the surface of the electrode. Since iron oxide scales are quite porous the attempt to passivate is easily overcome as the potentiostat raises the applied potential further.

Figure 4:
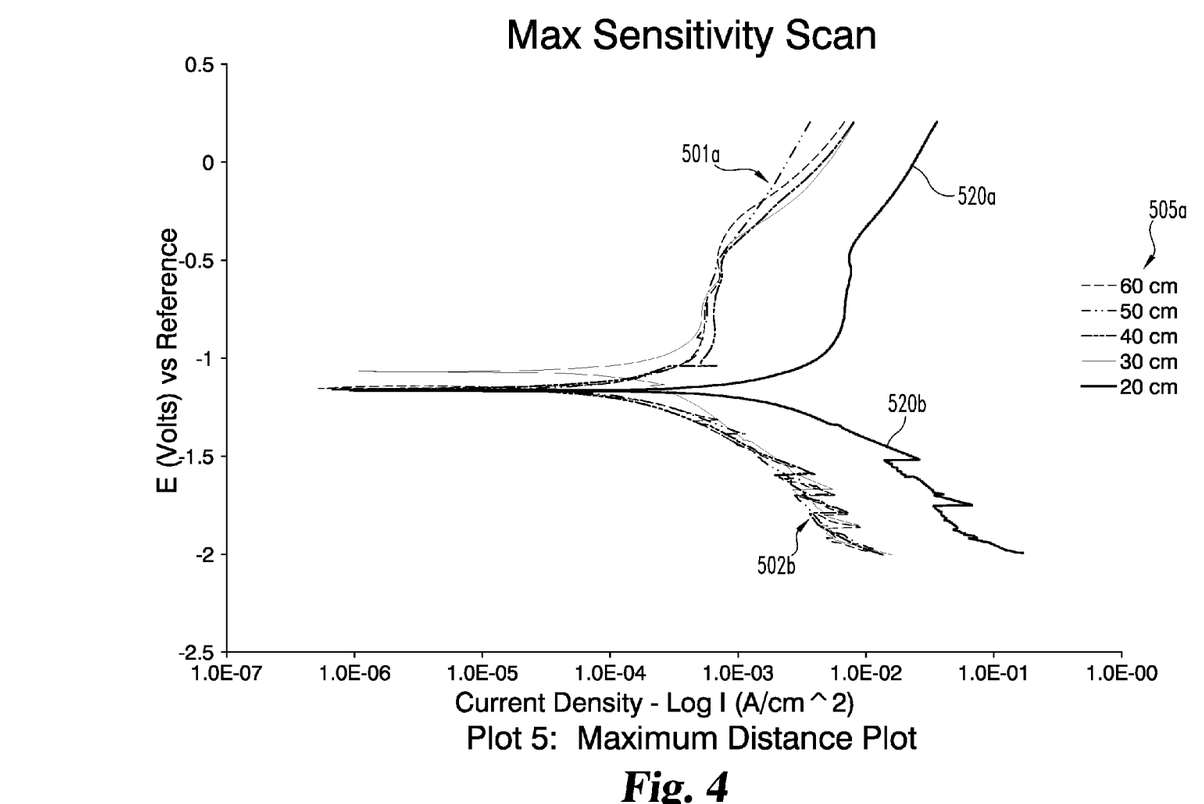
FIG. 4 is a Tafel plot showing scan distances from 20 cm to 60 cm.

In Table 4 it is shown that at 20 cm from the working electrode a current density of 5.0 E-2 A/cm$^2$ was noted and increased further to 9.0 E-1 A/cm$^2$ at 1 cm scan distance. The last scan plotted to the right is that of the laboratory reference electrode and it was used as comparison to verify the integrity of the collected data and measured 9.5 E-1 A/cm$^2$ 1 cm away from the working electrode. In FIG. 4 scans were taken starting at 60 cm and reduced by 10 cm each trial until a correlation between the previous scans which started at 20 cm was achieved. A comparative jump in the current density of the test was noted at 20 cm distance from the working electrode. This jump is illustrated in FIG. 4 by comparing plots 501a with 20 cm plot 520a, and comparing plots 502b with 20 cm plot 520b. This jump in nearly an order of magnitude greater may be considered approaching a limit of the electrodes general sensitivity, at least for the particular sample and conditions in this test.

From the collected data a correlation was made between the efficiency of the Pine system with an external electrode. It is noted that as the area of the working electrode increase there is a greater surface area required to plate nickel from solution. Since greater amounts of energy are required to carry the same current density on the surface of the electrode; by applying a fixed potential plating efficiency losses are expected and noted. As tested the prototype electrode displayed a surprising sensitivity. The collected current densities were representative of the anticipated response base on theory. Simply put the further you are away from the working electrode the greater the resistance therefore the greater the lower the values of current density generated.

The manufacturing techniques used to manufacture the prototype were quite simple and cost effective. Based on the sum of the materials purchased and an anticipated total manufacturing run from supplies purchased, the cost of a single electrode is estimated to be less than a dollar a piece. The maximum sensitivity of the prototype 210 was also noted as quite high. An erratic signal was not noted. As the distance between the electrodes decreased a sizable jump was noted in the recorded current densities at approximately 20 cm. From FIG. 4, the optimum general sensitivity of the electrode is thought to be best optimized at approximately 20 cm under the tested conditions.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. The examples, and the testing set forth above, are not the only version of the invention. Rather, the claims set forth the scope of the invention.

The invention claimed is:

1. A method for signal generating and collecting data to detect and evaluate corrosion in a conductive metal subject beneath a protective coating, comprising the acts of:
   a) providing a voltage generator;
   b) attaching a metallic conductor to at least one connection point with said conductive metal subject to electrically connect it to said voltage generator, wherein said conductive metal subject is a pipeline;
   c) providing a carrier having thereon an assembly of:
      i) a counter electrode electrically connected to said voltage generator; and,
      ii) a reference electrode electrically connected to said voltage generator;
   d) positioning said counter electrode and said reference electrode assembly in an electrolyte solution or wet carrier providing electrical conductivity between said counter electrode and said conductive metal subject beneath said protective coating with a voltage potential between it and said counter electrode, wherein said carrier and said counter electrode and said reference electrode are positioned not in direct physical contact with said conductive metal subject and yet within proximity of said conductive metal subject; and,
   e) providing a voltage potential through said electrolyte solution or wet carrier across said metallic conductor and said reference electrode;
   f) providing a first electrical signal from said voltage generator through an electrical circuit which includes said connection point and said conductive metal subject, said electrolyte solution or wet sponge, and said counter electrode;
   g) whereby said conductive metal subject becomes a working electrode; and
   h) collecting data from said first electrical signal and providing at least one display thereof to indicate corrosion of said conductive metal beneath said protective coating.

2. A method of claim 1, wherein said carrier comprises a printed circuit board.

3. A method of claim 2, wherein said carrier is readily removably mounted in a probe, wherein said probe is portable and operator hand-held and physically separate from the conductive metal subject.

4. A method of claim 3, and further comprising forming a small penetration in said protective coating sufficient to allow said electrolyte solution or wet carrier to contact said conductive metal.

5. A method of claim 4, wherein said first signal comprises an electrical signal having a voltage varied as a function of time.

6. A method of claim 5, wherein said voltage generator comprises a potentiostat and wherein said display comprises an electrochemical technique of current density variance as a function of voltage variance.

7. A method of claim 6, wherein said conductive metal is a portion of an underwater pipeline and wherein said electrolyte solution or wet carrier is seawater.

8. A method of claim 7, and further comprising providing a second electrical signal through an electrical circuit which includes said counter electrode and said reference electrode assembly, said electrolyte solution or wet carrier, and wherein said display comprises a Tafel plot of current density variance as a function of voltage variance of said second signal.

9. A method of claim 1, wherein said carrier is readily removably mounted in a probe, wherein said probe is portable and operator hand-held and physically separate from the conductive metal subject.

10. A method of claim 1, and further comprising forming a small penetration in said protective coating sufficient to allow said electrolyte solution or wet sponge to contact said conductive metal.

11. A method of claim 1, wherein said first signal comprises an electrical signal having a voltage varied as a function of time.

12. A method of claim 11, wherein said voltage generator comprises a potentiostat and wherein said display comprises an electrochemical technique of current density variance as a function of voltage variance.

13. A method of claim 11, and further comprising providing a second electrical signal through an electrical circuit which includes said counter electrode and said reference electrode assembly, said electrolyte solution or wet carrier, and wherein said display comprises a Tafel plot of current density variance as a function of voltage variance of said second signal.

14. A method of claim 1, wherein said conductive metal is a portion of an underwater pipeline and wherein said electrolyte solution is seawater.

15. The method of claim 1, wherein said counter electrode and said reference electrode are printed circuitry printed on said carrier.

16. The method of claim 1, wherein said carrier is positioned within about 100 centimeters from said conductive metal subject.

17. The method of claim 16, wherein said carrier is positioned within about 60 centimeters from said conductive metal subject.

18. The method of claim 1, wherein said carrier is moved along a length of said conductive metal subject, whereby penetrations in the protective coating are detected when said carrier passes in proximity to said penetrations and current passes between said working electrode and said counter electrode.

* * * * *